United States Patent [19]

Dvonch et al.

[11] 4,000,137
[45] Dec. 28, 1976

[54] ANTITUMOR DERIVATIVES OF PERIODATE-OXIDIZED NUCLEOSIDES

[75] Inventors: William Dvonch, Radnor; Harvey E. Alburn, West Chester, both of Pa.

[73] Assignee: American Home Products Corporation, New York, N.Y.

[22] Filed: June 10, 1975

[21] Appl. No.: 585,646

[52] U.S. Cl. .......................... 260/252; 260/251 R; 424/251; 424/253
[51] Int. Cl.² ............. C07D 473/00; C07D 239/04
[58] Field of Search ................................. 260/252

[56] References Cited

OTHER PUBLICATIONS

Cancer Research, 26, Part I, 2386–2389, (1966).

*Primary Examiner*—Lewis Gotts
*Assistant Examiner*—D. R. Phillips
*Attorney, Agent, or Firm*—David E. Frankhouser

[57] ABSTRACT

The reaction of the periodate oxidation product from inosine, adenosine, or cytidine with methanol or ethanol affords a product having activity against lymphocytic leukemia P388 in mice.

5 Claims, No Drawings

ANTITUMOR DERIVATIVES OF PERIODATE-OXIDIZED NUCLEOSIDES

The periodate oxidation products of various nucleosides having antitumor activity are described by Dvonch et al., *Cancer Research*, 26, 2386 (1966). The addition of methanol or ethanol to periodate-oxidized glycosides is disclosed by Goldstein et al., *Chem. and Ind.*, page 595 (May 17, 1958). The Goldstein publication does not, however, disclose addition products of periodate-oxidized nucleosides, and no utility for the addition products is taught.

In accordance with the present invention there are provided chemical compounds of the formula:

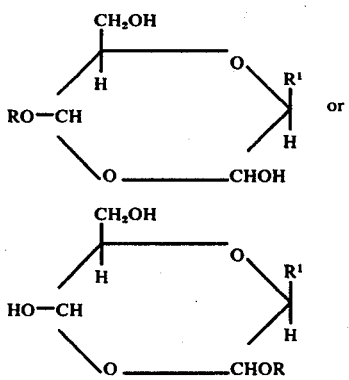

wherein R is methyl or ethyl and $R^1$ is a group selected from

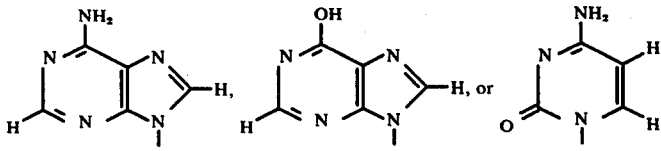

The compounds of Formula I or II, wherein R and $R^1$ are as hereinbefore defined, inhibit lymphocytic leukemia P388 in mice when tested according to the standard assay procedure described in *Cancer Chemotherapy Reports*, Volume 3, No. 2, p. 9 (Protocol 1.200), September, 1972.

The compounds of Formula I or II are prepared by dissolving an appropriate periodate-oxidized nucleoside in methanol or ethanol at ambient temperatures. The product may be recovered by concentrating the solution to a small volume, adding an equal volume of ether, and allowing the solution to stand in the cold (for example, at 5° C) until precipitation is complete. The precipitate is isolated by conventional procedures.

The starting periodate-oxidized nucleosides are known compounds. Those from adenosine and cytidine are described in the Dvonch article, supra, or in U.S. Pat. No. 3,388,115. The periodate-oxidation product from inosine is described by Lictenthaler et al., *Chem. Ber.*, 99, 585 (1966). Although Lictenthaler isolated the product in the presence of methanol, the product is described as having the dialdehyde structure.

Periodate-oxidation products are usually represented as a dialdehyde, as illustrated below in Formula III. In solution, however, the dialdehyde may be in equilibrium with other forms, notably the monaldehyde (IV) through hemiacetal formation.

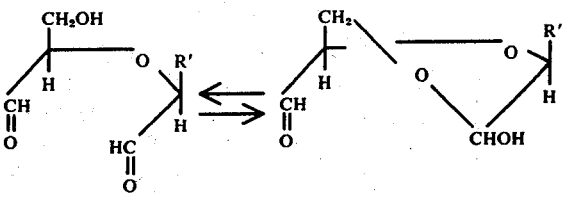

Other forms are theoretically possible [see Guthrie, *Advanced Carbohydrate Chem.*, 16, 105 (1961)]. As used herein, the term "periodate-oxidation product" means the dialdehyde form and the other forms in equilibrium therewith.

In the reaction of methanol or ethanol with the periodate-oxidation product, the alcohol adds to the aldehyde groups to ultimately form a cyclic structure. Depending upon the initial site of reaction, two position isomers (Formula I or II) are possible. The product is normally isolated as a mixture of the two position isomers, but, if desired, the isomers can be separated by conventional procedures. In the examples hereinafter described and in the claims, the compounds are named to represent a mixture of the two position isomers.

It will be apparent to those skilled in the art that the compounds of Formula I and II possess asymmetric carbon atoms and, hence, optical isomers are possible. All optical isomers or mixtures thereof are, therefore, represented by the structural formulae depicted herein and are intended to be included within the scope of the present invention.

The following examples illustrate the processes of this invention.

EXAMPLE I

9-[3(5)-Hydroxy-6-Hydroxymethyl-5(3)-Methoxy-p-Dioxan-2-Yl]-9H-Purin-6-ol

Inosine (5.02 g; 18.7 mmoles) was oxidized with 0.1 M periodic acid solution (206 ml.; 20.6 mmoles) for 2 hr. at room temperature in the dark. The solution was passed over a Dowex 1-X8-acetate column (32 ml. volume), and the column was washed with water. The self-eluate and the wash were combined and freeze dried to give the amorphous periodate-oxidation product. This material was dissolved in methanol (150 ml.), concentrated to a small volume (20 ml.), and dried in vacuo to give the title product as the hemihydrate.

Analysis for: $C_{11}H_{14}N_4O_6$; 0.50 $H_2O$; 0.34 AcOH: Calculated: C, 42.63; H, 5.42; N, 17.02. Found: C, 42.81; H, 5.03; N, 17.10.

A T/C of 210% was found for this compound in mice vs. P-388 leukemia at 120 mg/kg in the standard NIH assay.

EXAMPLE II

9-[3(5)-Ethoxy-5(3)-Hydroxy-6-Hydroxymethyl-p-Dioxan-2-Yl]-9H-Purin-6-ol

Inosine periodate-oxidation product (3 g.) was dissolved in ethanol (250 ml.), concentrated to a small volume (25 ml.); and ether (25 ml.) was added. The mixture was stored at 5° overnight, and the product was filtered off and dried in vacuo to give the title product (1.9 g.) as the hemihydrate.

Analysis for: $C_{12}H_{16}N_4O_6 \cdot \frac{1}{2} H_2O$: Calculated: C, 44.90; H, 5.34; N, 17.45. Found: C, 44.88; H, 5.44; N, 17.03.

A T/C of 217% was found for this compound in mice vs. P-388 leukemia at 120 mg/kg in the standard NIH assay.

EXAMPLE III

6-Amino-9-[3(5)-Hydroxy-6-Hydroxymethyl-5(3)-Methoxy-p-Dioxan-2-Yl]-9H-Purine Adenosine periodate-oxidation product was treated with methanol according to the procedure of Example I to give the title product as the hemihydrate.

Analysis for: $C_{11}H_{15}N_5O_5 \cdot \frac{1}{2} H_2O$: Calculated: C, 43.15; H, 5.26; N, 22.85. Found: C, 42.83; H, 5.10; N, 22.71.

A T/C of 168% was found for this compound in mice vs. P-388 leukemia at 20 mg/kg in the standard NIH assay.

EXAMPLE IV

6-Amino-[3(5)-Ethoxy-5(3)-Hydroxy-6-Hydroxymethyl-p-Dioxane-2-Yl]-9H Purine

Adenosine periodate-oxidation product was treated with ethanol according to the procedure of Example II to give the title compound as the hydrate.

Analysis for: $C_{12}H_{17}N_5O_6 \cdot H_2O$: Calculated: C, 43.76; H, 5.82; N, 21.27. Found: C, 43.85; H, 5.29; N, 21.60.

A T/C of 149% was found for this compound in mice vs. P-388 leukemia at 20 mg/kg in the standard NIH assay.

EXAMPLE V

4-Amino-1-[3(5)-Hydroxy-6-Hydroxymethyl-5(3)-Methoxy-p-Dioxan-2-Yl]-2H-Pyrimidin-2-One Cytidine periodate-oxidation product was treated with methanol according to the procedure of Example I to give the title product as the hemihydrate.

Analysis for: $C_{10}H_{15}N_3O_6 \cdot \frac{1}{2} H_2O$: Calculated: C, 42.60; H, 5.72; N, 14.97. Found: C, 42.41; H, 5.63; N, 14.49.

A T/C of 165% was found for this compound in mice vs. P-388 leukemia at 120 mg/kg in the standard NIH assay.

EXAMPLE VI

4-Amino-1-[3(5)-Ethoxy-5(3)Hydroxy-6-Hydroxymethyl-p-Dioxan-2-Yl]-2H-Pyrimidin-2-One Cytidine periodate-oxidation product (2.0 g.) was dissolved in ethanol (250 ml.), and the solution was concentrated to a small volume (25 ml.). An equal volume of ether was added, and the mixture was stored at 5° to crystallize the product as the hydrate (1.0 g.).

Analysis for: $C_{11}H_{17}N_3O_6 \cdot H_2O$: Calculated: C, 43.28; H, 6.26; N, 13.75. Found: C, 43.13; H, 5.73; N, 13.61.

A T/C of 173% was found for this compound in mice vs. P-388 leukemia at 60 mg/kg in the standard NIH assay.

What is claimed is:

1. A compound of the formula

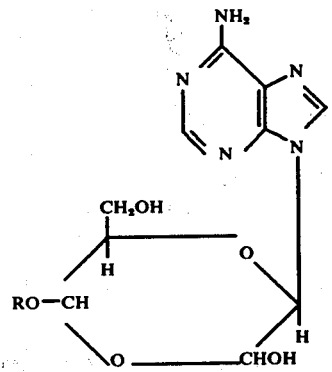

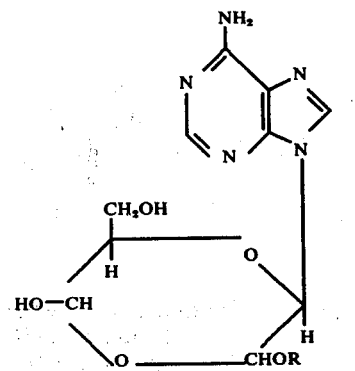

wherein R is methyl or ethyl.

2. A compound as defined in claim 1 which is 9-[3(5)-hydroxy-6-hydroxymethyl-5(3)-methoxy-p-dioxan-2-yl]-9H-purin-6-ol.

3. A compound as defined in claim 1 which is 9-[3(5)-ethoxy-5(3)-hydroxy-6-hydroxymethyl-p-dioxan-2-yl]-9H-purin-6-ol.

4. A compound as defined in claim 1 which is 6-amino-9-[3(5)-hydroxy-6-hydroxymethyl-6(3)-methoxy-p-dioxan-2-yl]-9H-purine.

5. A compound as defined in claim 1 which is 6-amino-[3(5)-ethoxy-5(3)-hydroxy-6-hydroxymethyl-p-dioxane-2-yl]-9H-purine.

* * * * *